(12) United States Patent
Lee (10) Patent No.: US 11,832,637 B2
(45) Date of Patent: Dec. 5, 2023

(54) SMART SYSTEM AND METHOD FOR PROVIDING INFORMATION ABOUT GREEN VEGETABLE JUICE

(71) Applicant: ANGEL Co., Ltd., Busan (KR)

(72) Inventor: Kwang Hui Lee, Busan (KR)

(73) Assignee: ANGEL Co., Ltd., Busan (KR)

( * ) Notice: Subject to any disclaimer, the term of this patent is extended or adjusted under 35 U.S.C. 154(b) by 0 days.

(21) Appl. No.: 17/578,892

(22) Filed: Jan. 19, 2022

(65) Prior Publication Data

US 2022/0225641 A1 Jul. 21, 2022

(30) Foreign Application Priority Data

Jan. 21, 2021 (KR) .................. 10-2021-0008574

(51) Int. Cl.
*A23L 2/04* (2006.01)
*G06V 20/68* (2022.01)
*G01N 33/02* (2006.01)

(52) U.S. Cl.
CPC .............. *A23L 2/04* (2013.01); *G01N 33/025* (2013.01); *G06V 20/68* (2022.01)

(58) Field of Classification Search
CPC ........ A23L 2/04; G06V 20/68; G06Q 10/087; G06Q 10/0875; G01N 33/025
USPC ......... 99/455, 467, 468, 470, 474, 485, 486, 99/517
See application file for complete search history.

(56) References Cited

U.S. PATENT DOCUMENTS

| 2013/0067375 | A1 | 3/2013 | Kim et al. |
| 2019/0164116 | A1* | 5/2019 | Wallace ................. G06V 20/20 |
| 2020/0342781 | A1 | 10/2020 | Kraut-Reinkober et al. |
| 2020/0357083 | A1 | 11/2020 | Wallace |

FOREIGN PATENT DOCUMENTS

| KR | 20180023080 A | 3/2018 |
| KR | 20190031649 A | 3/2019 |
| KR | 20190100525 A | 8/2019 |
| KR | 20210069860 A | 6/2021 |

* cited by examiner

*Primary Examiner* — Phuong T Nguyen
(74) *Attorney, Agent, or Firm* — Bridgeway IP Law Group, PLLC; Jihun Kim (57) ABSTRACT

Proposed is a smart method of providing information about green vegetable juice, the method including: obtaining juice-extraction information which includes information about juice-extraction time of the green vegetable juice, information about weight of the green vegetable juice, and information about ingredients for the green vegetable juice; receiving intake information about the green vegetable juice from a user; calculating change in the weight and freshness of stored green vegetable juice based on the juice-extraction information and the intake information; and generating and displaying a smart button with status information about the stored green vegetable juice based on the calculated change in the weight and freshness of the green vegetable juice. By this method, it is possible to intuitively know the weight and the freshness of the stored green vegetable juice.

3 Claims, 6 Drawing Sheets

SMART SYSTEM AND METHOD FOR PROVIDING INFORMATION ABOUT GREEN VEGETABLE JUICE

CROSS-REFERENCE TO RELATED THE APPLICATION

This application is based on and claims priority under 35 U.S.C. § 119 to Korean Patent Application No. 10-2021-0008574 filed on Jan. 21, 2021, in the Korean Intellectual Property Office, the disclosure of which is incorporated by reference herein in its entirety.

BACKGROUND

Field

The disclosure relates to a smart system and method for providing information about green vegetable juice, and more particularly to a smart system and method for providing information about green vegetable juice, i.e., information about a status of green vegetable juice in storage.

Description of the Related Art

In this specification, a juicer for green vegetable juice will be used as a concept of encompassing all devices capable of making green vegetable juice with various ingredients such as vegetables, fruits, seeds, etc. Therefore, the juicer for green vegetable juice in this embodiment encompasses devices variously named 'blender,' 'mixer,' 'slow juicer,' 'juice extractor,' etc.

The juicer for green vegetable juice has been sold as a device with compact hardware and software for making the green vegetable juice. For example, the juicer for green vegetable juice with only a compact structure of a blade, a motor, a user interface, a driving microcomputer, etc. may be used by a user to make desired green vegetable juice in person.

However, it is known that the juicer for green vegetable juice is very cumbersome to clean after use because residues get stuck in components during a juicing process. Therefore, instead of using the juicer for green vegetable juice every day, it is usual for users to extract juice as much as they can drink for several days at a time and store the juice in a freezer or refrigerator as subdivided.

Further, there are various ingredients for green vegetable juice, which are different in shelf life, and the juice is generally extracted from not a single ingredient but a plurality of ingredients. Therefore, when painstakingly extracted green vegetable juice is not carefully preserved during storage or thawing, there are serious problems that the juice goes bad or its nutrients are destroyed.

SUMMARY

To solve the foregoing problems, an aspect of the disclosure is to provide a smart system and method for providing information about green vegetable juice, in which the amount and freshness of stored green vegetable juice are calculated and a user is allowed to intuitively know the amount and freshness.

Further, an aspect of the disclosure is to provide a smart system and method for providing information about green vegetable juice, in which an indicator ingredient having representativeness is selected among ingredients for green vegetable juice, and the freshness and remaining shelf life of the green vegetable juice are calculated based on a freshness changing function of the indicator ingredient, thereby simply and accurately reflecting the freshness of the green vegetable juice.

According to an embodiment of the disclosure, there is provided a smart method of providing information about green vegetable juice, the method including: obtaining juice-extraction information which includes information about juice-extraction time of the green vegetable juice, information about weight of the green vegetable juice, and information about ingredients for the green vegetable juice; receiving intake information about the green vegetable juice from a user; calculating change in the weight and freshness of stored green vegetable juice based on the juice-extraction information and the intake information; and generating and displaying a smart button with status information about the stored green vegetable juice based on the calculated change in the weight and freshness of the green vegetable juice.

The calculating the change in the freshness of the green vegetable juice may include: selecting at least one among the ingredients for green vegetable juice as an indicator ingredient; and calculating a freshness value and a remaining shelf life of the green vegetable juice depending on a storage period of the green vegetable juice or the storage period and a storage temperature based on a freshness changing function of the indicator ingredient.

In addition, the smart button may include a freshness display area for indicating the freshness of the green vegetable juice, and a remaining-life display area indicating the remaining shelf life; and the generating and displaying the smart button may include determining and displaying a color of the freshness display area based on the calculated freshness value.

Further, the smart button may include a colored area in the freshness display area, which is displayed to be changed in size in proportion to the weight of the stored green vegetable juice.

Furthermore, the information about the juice-extraction time of the green vegetable juice and the information about the weight of the green vegetable juice may be received from a juicer for extracting the green vegetable juice, and the information about the ingredients for the green vegetable juice may be received from at least one of the juicer and a service server.

Further, the method may further include receiving recipe information about the green vegetable juice from a service server, wherein the obtaining the juice-extraction information includes obtaining information about the ingredients for green vegetable juice from the recipe information.

Meanwhile, the method may further include identifying ingredients to be put for green vegetable juice by an image sensor in a juicer for green vegetable juice, wherein the obtaining the juice-extraction information includes receiving identification information about the ingredients for green vegetable juice from the juicer for green vegetable juice.

Here, the method may further include calculating the weight of the green vegetable juice by determining the weight of the ingredients for green vegetable juice by the image sensor in the juicer for green vegetable juice, wherein the obtaining the juice-extraction information includes receiving information about the weight of the green vegetable juice from the juicer for green vegetable juice.

In addition, the receiving the intake information about the green vegetable juice may include generating a user interface to receive an input about intake of the green vegetable juice, and the calculating the weight of the green vegetable juice may include reducing the weight of the stored green vegetable juice based on the input about the intake of the green vegetable juice.

Meanwhile, according to an embodiment of the disclosure, there is provided a smart system for providing information about green vegetable juice, the system including: a juicer for green vegetable juice, configured to extract juice from ingredients for green vegetable juice, and generate and transmit juice-extraction information which includes information about juice-extraction time of the green vegetable juice and information about weight of the green vegetable juice; and a user terminal configured to receive the juice-extraction information from the juicer for green vegetable juice, receive intake information about the green vegetable juice from a user, and generate and display a smart button with status information about the stored green vegetable juice depending on change in the weight and freshness of stored green vegetable juice based on the juice-extraction information and the intake information.

Here, the system may further include a service server configured to generate recipe information about the green vegetable juice and provide the recipe information to at least one of the user terminal and the juicer for green vegetable juice, wherein the user terminal receives the recipe information from the service server or the juicer for green vegetable juice, and obtains information about the ingredients for green vegetable juice based on the recipe information.

In addition, at least one of the service server and the user terminal selects at least one among the ingredients for green vegetable juice as an indicator ingredient, and calculates a freshness value and a remaining shelf life of the green vegetable juice depending on a storage period of the green vegetable juice or the storage period and a storage temperature based on a freshness changing function of the indicator ingredient.

Further, the smart button may include a freshness display area for indicating the freshness of the green vegetable juice, and a remaining-life display area indicating the remaining shelf life; and the user terminal may determine and display a color of the freshness display area based on the calculated freshness value.

In addition, the user terminal may generate a user interface to receive an input about intake of the green vegetable juice, calculate the weight of the stored green vegetable juice based on the input about the intake of the green vegetable juice, and reduce a colored area in the freshness display area of the smart button in size in proportion to the calculated weight of the stored green vegetable juice.

BRIEF DESCRIPTION OF THE DRAWINGS

The above and/or other aspects will become apparent and more readily appreciated from the following description of embodiments, taken in conjunction with the accompanying drawings, in which.

DETAILED DESCRIPTION OF EMBODIMENTS

Below, exemplary embodiments of the disclosure will be described with reference to the accompanying drawings.

Figure 1:
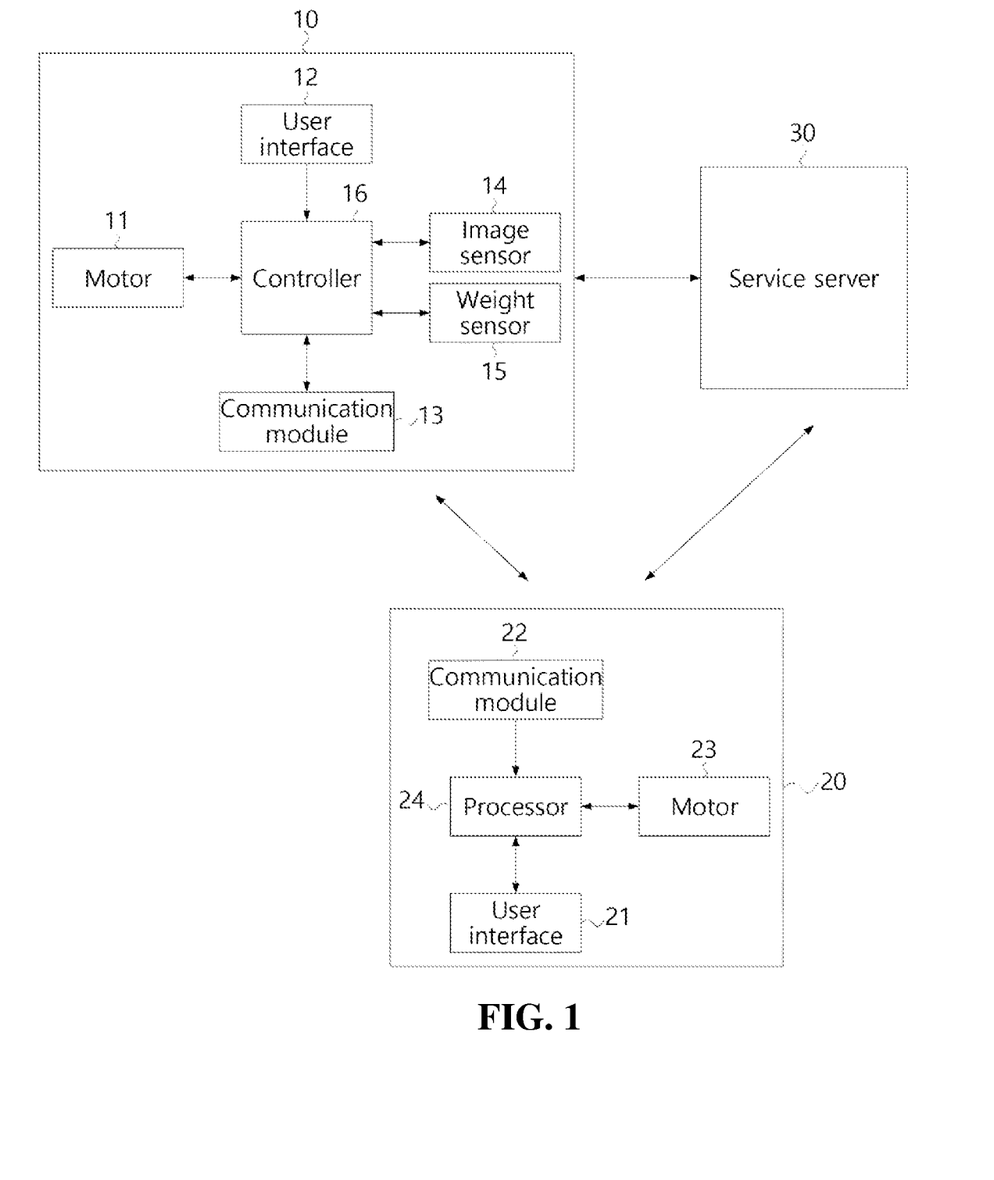
FIG. 1 is a block diagram of a smart system for providing information about green vegetable juice according to a first embodiment of the disclosure.

FIG. 1 is a block diagram of a smart system for providing information about green vegetable juice according to a first embodiment of the disclosure. Referring to FIG. 1, a smart system for providing information about green vegetable juice according to an embodiment of the disclosure includes a juicer 10 for green vegetable juice, a user terminal 20, and a service server 30.

The juicer 10 for green vegetable juice encompasses devices capable of making the green vegetable juice by griding and juicing ingredients for the green vegetable juice, and thus includes a screw or blade, a motor 11, a user interface 12, a communication module 13, etc., which are provided in a juice extractor, a blender or the like existing device as it is well known.

For example, the juicer 10 for green vegetable juice according to an embodiment of the disclosure may include a pressurizing gear, a juicing means spirally formed with a screw, and the motor 11 with a decelerator, in which the juicing means is connected to the output shaft of the decelerator, turns based actuation of the motor 11, and extracts juice from the ingredients for green vegetable juice. The user interface 12 may further include an input means such as a button, a keypad or the like for receiving an information input, and a display means such as a liquid crystal display (LCD) or the like for displaying various pieces of information, for example, an input menu, a process result, etc. The communication module 13 is configured to communicate with the user terminal 20 and/or the service server 30, and may be embodied by various communication modules based on Wi-Fi, Bluetooth, near field communication (NFC), Zigbee, infrared ray (IR), radio frequency (RF), etc.

Referring to FIG. 1, the juicer 10 for green vegetable juice according to the first embodiment of the disclosure may further include an image sensor 14, a weight sensor 15, and a controller 16. The image sensor 14 is configured to capture an image of ingredients for green vegetable juice, and may be embodied by a complementary metal-oxide semiconductor (CMOS), a charge-coupled device (CCD), a camera, or the like. The weight sensor 15 is configured to measure the weight of the green vegetable juice, and may be embodied by a scale with a load cell, etc. The controller 16 is configured to control overall operations of the juicer 10 for green vegetable juice and analyze and process juice-extraction information about the juicer 10 for green vegetable juice, and may include a memory stored with data and software, an input/output device (peripherals), etc. in addition to a processing module for processing data. The controller 16 may run the software stored in the memory to control another element (e.g., a hardware or software element) connected to the controller 16 and perform various types of data processing and operation. The controller 16 may load and process an instruction or data received from another element (e.g., the communication module) to a volatile memory, and store result data in a nonvolatile memory. The controller 16 further includes a clock, a timer or the like to obtain juice-extraction time information.

The juicer 10 for green vegetable juice according to an embodiment of the disclosure is characterized in having a function of generating the juice-extraction information. Here, the juice-extraction information may include one or more among information about the weight of the ingredients for green vegetable juice, information about the weight of the green vegetable juice after juice extraction, information about time taken in the juice extraction, information about the identification of the ingredients for green vegetable juice, a mixing ratio of multiple ingredients for green vegetable juice, juice-extraction conditions (temperature, witteness, the rotational force of the motor, the rotational profile of the motor according to time, applied pressure, the clearance of the screw, the clearance of the pressurizing gear, etc.) and the like information.

Some data of the juice-extraction information is determined based on control software of the juicer 10 for green vegetable juice, and thus the rotational force of the motor, the profile of the motor, the clearance of the screw, the clearance of the gear, and the like juice-extraction conditions may be obtained from the juicer 10 itself for green vegetable juice. In addition, the information about time taken in the juice extraction may be obtained from the clock or timer provided in the juicer 10 for green vegetable juice.

Among the pieces of juice-extraction information, the information about the ingredients for green vegetable juice may be obtained from an Internet of things (IoT) sensor and the like peripherals and provided to the controller 16. Here, the peripherals may be a part of the juicer 10 for green vegetable juice, or may be provided separately from and connected to the juicer 10 for green vegetable juice through wired/wireless data communication. The IoT sensor may include a separate identification sensor for identifying the ingredients for green vegetable juice, an image sensor, a weight sensor, etc.

For example, the images of the ingredients for green vegetable juice may be obtained through the image sensor 14, and the controller 16 analyzes the images to thereby identify the ingredients to be put for green vegetable juice. To identify the ingredients for green vegetable juice based on image analysis, the images of the ingredients for green vegetable juice may be previously stored, and then identified based on various well-known algorithms that derive shapes and colors from the pixels of the images. Alternatively, the identification information about the ingredients for green vegetable juice may be obtained by applying the images of the image sensor 14 to an artificial intelligence (AI) model which has been established by learning about the shapes corresponding to the ingredients for green vegetable juice based on deep learning techniques. The AI-based object identification algorithm has already been implemented through work robots and sensors in a food field and a farm, and thus does not have any special exclusivity as the well-known art so that the embodiments of the disclosure can be realized without being particularly restricted thereto.

The weight information about the ingredients for green vegetable juice or the weight information about the green vegetable juice after the juice extraction may be obtained by directly measuring the weight of the ingredients for green vegetable juice or the weight of the green vegetable juice, or may be inferred. The weight sensor 15 for measuring the weight may be provided in such a manner that the load cell is installed under a hopper into which the ingredients for green vegetable juice are put. Alternatively, the weight sensor 15 may directly measure the weight of the ingredients before putting the ingredients into the hopper, or may directly measure the weight of the green vegetable juice after the juice extraction. Alternatively, the controller 16 may estimate the volume of the ingredients by analyzing a shape image of ingredients captured by the image sensor 14 based on the foregoing AI-based learning, and infer the weight of the ingredients for green vegetable juice or the weight of the green vegetable juice based on the estimated volume. In terms of AI-based algorithms, various learning techniques may be optimally selected and applied to an application field. For example, a deep learning technique may be used for the image analysis of the ingredients for green vegetable juice, and a reinforcement learning technique may be used for weight inference.

To obtain the identification information about the ingredients for green vegetable juice, a partition wall for each ingredient is provided in the hopper into which the ingredients for green vegetable juice are put, so that images can be captured and analyzed according to spaces partitioned by the partition walls while the images are captured by the image sensor 14. Besides, to obtain the weight information about the ingredients for green vegetable juice, there may be used a container (not shown) in which load cells are distributed and installed to separately calculate the whole weight and the weight corresponding to each partitioned space. Here, the container (not shown) may include a communication module for providing the measured weight information to the controller 16 through wired/wireless communication. Here, the weight of the green vegetable juice after the juice extraction may be directly measured by the load cells installed on the bottom of the container, or may be inferred from the weight of the ingredients for green vegetable juice.

Meanwhile, the juice-extraction information may be partially obtained by a user's direct input and by data communication with an external device, and the obtained information may be combined by the controller 16.

The controller 16 may obtain the juice-extraction information through the IoT sensor, some components (e.g., the clock), internal control parameters, data communication with the external device, a user's direct input, etc. according to data attributes of the juice-extraction information, and combines the juice-extraction information. Further, the obtained juice-extraction information is transmitted to the user terminal 20 and/or the service server 30.

The user terminal 20 may include a user interface 21, a communication module 22, a memory 23, and a processor 24. The user terminal 20 may be embodied by any computing device capable of performing communication, such as a mobile phone, a tablet, a personal computer (PC), etc. The user terminal 20 may be installed with a user application for receiving services according to embodiments of the disclosure. For example, the user terminal 20 may communicate with the service server 30 under control of the application, and receive a service provided by the service server 30. The user application installed in the user terminal 20 may be classified into an application for a mobile terminal, and a web application for the PC.

Meanwhile, a file distribution server may be provided to distribute files for installation of the user application. For example, the file distribution server may store and manage the files and provide the stored file to the user terminal 20 as requested by the user terminal 20, and the user terminal 20 may be installed with the application based on the file provided by the file distribution server and receive the service through the installed user application. The file distribution server may be a server included in the service server 30, but may be a server linked to the serviced server 30 as a server of a third party.

The user interface 21 is configured to interact with a user, and may be embodied including a mouse, a keyboard, a button, a keypad, and the like input means for inputting information; and a display, e.g., an LCD, or the like for displaying various images and information such as an input menu, a processing result, etc.

The communication module 22 is for data communication with an external device to collaboratively process data, and may be embodied by various communication modules based on long term evolution (LTE), fifth generation mobile communications (5G), Wi-Fi, Bluetooth, NFC, Zigbee, IR, RF, etc.

The memory 23 is configured to store various pieces of data and software, and the user application according to the disclosure, and may include a volatile memory and a nonvolatile memory.

The processor 24 is configured to execute the user application stored in the memory 23 and analyze and process data. Specifically, the processor 24 may drive the user application stored in the memory 23 to control another element (e.g., hardware or software) connected to the processor 24, and perform various types of data processing and operation. The processor 24 may process an instruction or data received from another element (e.g., the communication module) by loading it to the volatile memory 23, and store result data in the nonvolatile memory 23.

The processor 24 receives the juice-extraction information from the juicer 10 for green vegetable juice, receives information about intake of the green vegetable juice from a user, and calculates change in the weight and the freshness value of the stored green vegetable juice based on the juice-extraction information and the intake information. In addition, the processor 24 generates information about the status of the stored green vegetable juice by a smart button based on the calculated weight and freshness value of the stored green vegetable juice, and controls the user interface 21 to display the generated information.

The processor 24 may select at least one among the ingredients for green vegetable juice as the indicator ingredient, and calculate the freshness value of the green vegetable juice according to the storage period of the green vegetable juice or calculate the freshness value of the green vegetable juice according to the storage period and the storage temperature, based on a freshness changing function of the indicator ingredient.

Further, the processor 24 may calculate the remaining shelf life as well as the freshness value of the green vegetable juice. Furthermore, the processor 24 may generate a push alarm for asking a user whether to intake the green vegetable juice, displays the push alarm on the user interface 21, and calculates the weight of the stored green vegetable juice by subtracting the amount of intake from the weight of the stored green vegetable juice when the user inputs selection about the intake. Here, the push alarm for asking whether to intake the green vegetable juice may be generated at a certain time every day. When the juice-extraction information is received from the juicer 10 for green vegetable juice, for example, when juice extraction is performed, the push alarm may be immediately generated to ask a user whether to intake the juice. When a user inputs that s/he drank the green vegetable juice, the push alarm is not generated and displayed on the same day. On the other hand, when a user inputs that s/he did not drank the green vegetable juice, the push alarm may be generated and displayed again.

The stored freshness value, the remaining shelf life, and the weight of the green vegetable juice, which are calculated by the processor 24, are provided to a user through the user interface 21.

According to an embodiment of the disclosure, the user terminal 20 (the user application) is characterized in informing a user of the state information of the stored green vegetable juice, for example, weight, freshness, the date of juice extraction, a remaining shelf life, ingredients, etc. by interworking with the juicer 10 for green vegetable juice. A user can check the weight, the freshness, the remaining shelf life, the ingredients, etc. of the green vegetable juice through the user application without opening a place for storing the green vegetable juice, e.g., a refrigerator, and thus easily manage the intake of the stored green vegetable juice.

The service server 30 is configured to provide resources needed for data processing of which information storage and calculation load are large. Specifically, the server 30 may include a memory configured to store resources, i.e., AI software for generating and recommending a customized recipe for green vegetable juice based on personal information about a user's health conditions; a high-specification processor for running the AI software; a communication module for data communication with the user terminal 20; etc. The service server 30 may transmit a customized recipe for green vegetable juice to the user terminal 20 and/or the juicer 10 for green vegetable juice.

Figure 2:
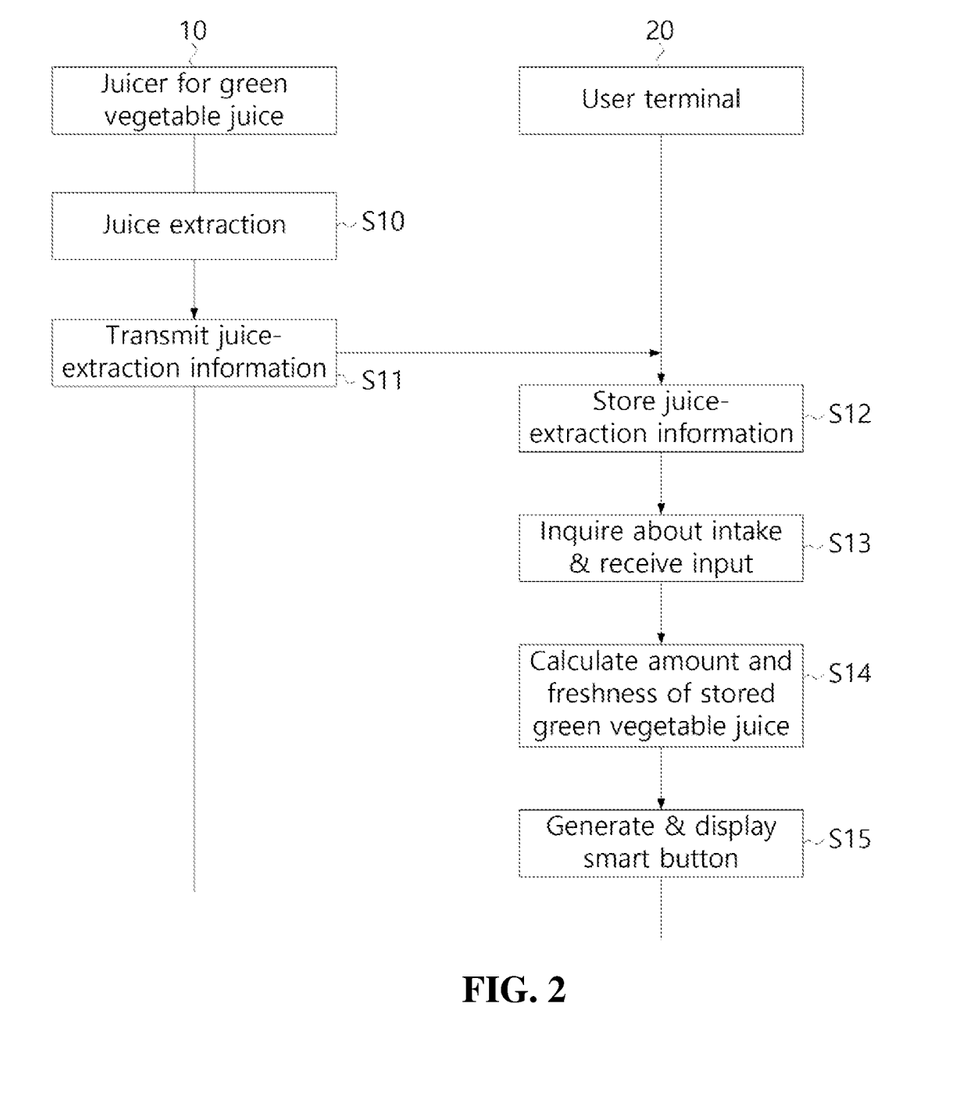
FIG. 2 is a flowchart showing an example of a smart method of providing information about green vegetable juice in the smart system of FIG. 1.
Figure 3:
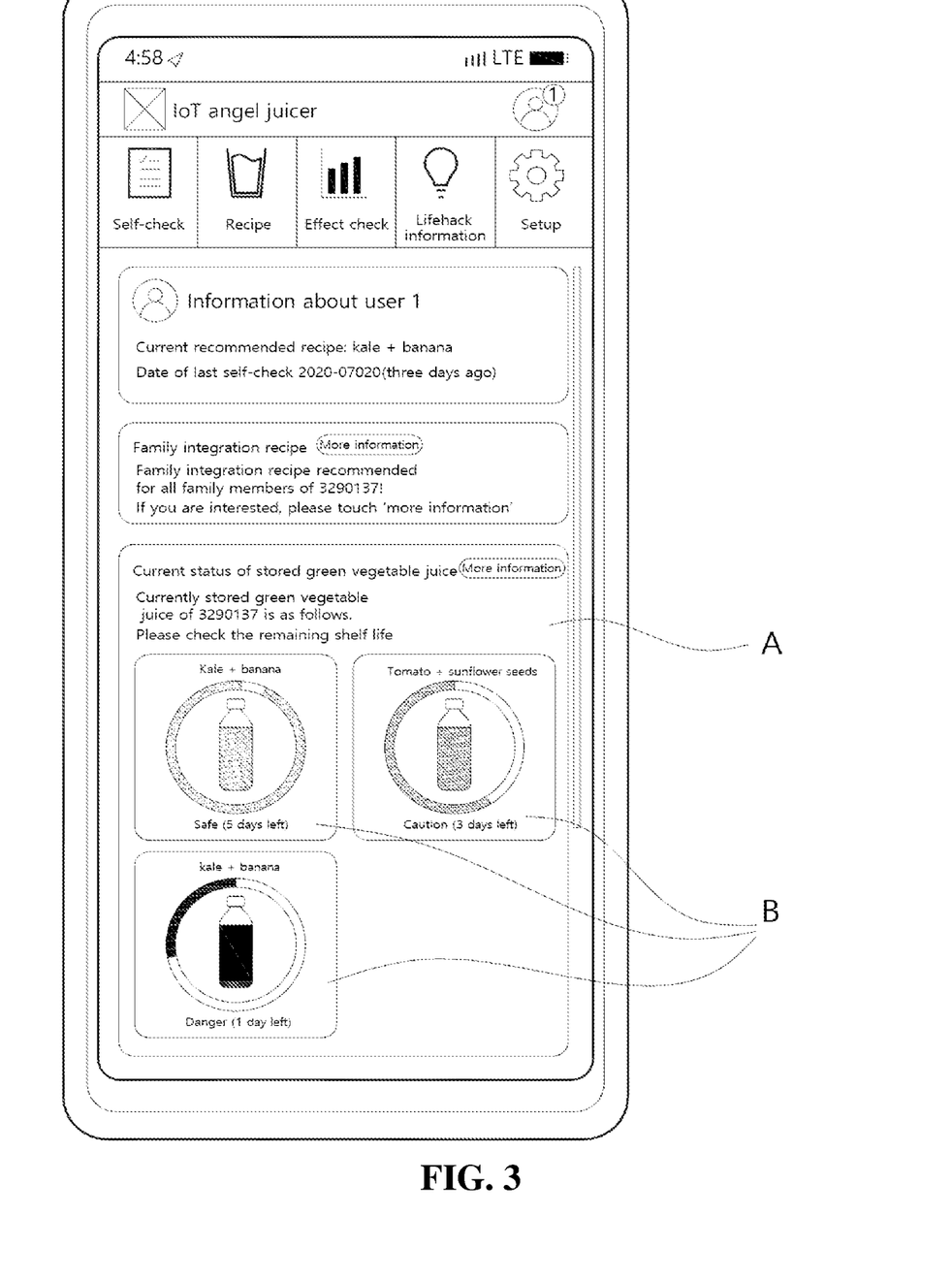
FIGS. 3 and 4 illustrate examples of a screen provided on a user terminal.
Figure 4:
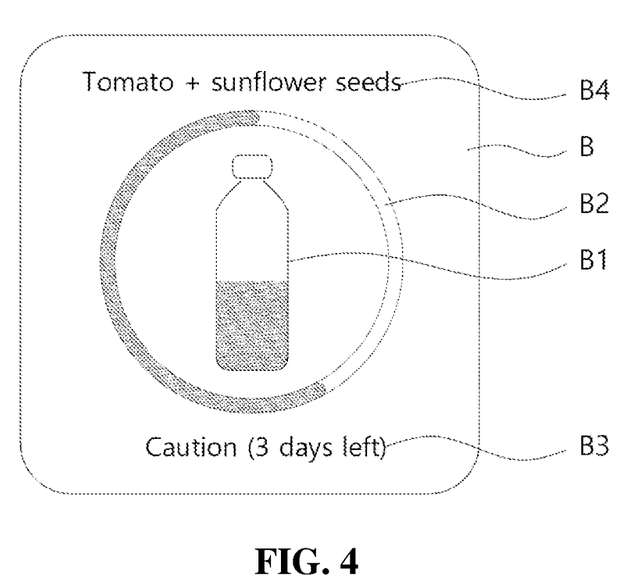

Below, a smart method of providing information about green vegetable juice according to the first embodiment of the disclosure will be described with reference to FIG. 2. FIG. 2 is a flowchart showing an example of a smart method of providing information about green vegetable juice in the smart system of FIG. 1, and FIGS. 3 and 4 illustrate examples of a screen provided on a user terminal;

A user may download and install an application related to a smart service for providing information about green vegetable juice according to the disclosure through the user terminal 20. A user may download the application by accessing the file distribution server or download the application transmitted from a specific site or a specific person. In this embodiment, installation of an app for a mobile terminal will be described by way of example. To receive a service, a user executes the application installed in the user terminal 20, signs up a membership and inputs login information, and the service server 30 performs membership registration based on the input information and performs a user's login authentication.

Referring to FIG. 2, when juice is extracted in the juicer 10 for green vegetable juice (S10), the juicer 10 for green vegetable juice obtains juice-extraction information, e.g., juice-extraction information which includes information about the juice-extraction time, information about the weight of the green vegetable juice, and information about the ingredients for green vegetable juice, and transmits the juice-extraction information to the user terminal 20 (S11).

The user terminal 20 stores the juice-extraction information transmitted from the juicer 10 for green vegetable juice (S12), generates and displays the push alarm for receiving intake information about the green vegetable juice from a user, and receives a user's selection about whether the user drank the green vegetable juice (S13). Because a user usually drinks the green vegetable juice immediately after the juice extraction, the push alarm according to this embodiment is generated and displayed immediately after the juice extraction to receive a user's input.

The push alarm generated immediately after the juice extraction may be designed to be different from the push alarm generated at a certain time every day. For example, a user usually drinks the green vegetable juice immediately after the juice extraction, and therefore a procedure may be completed when a button for getting confirmation of only the intake by an input such as 'Yes,' 'No,' etc. is generated and the input is made. On the other hand, the push alarm generated at a certain time every day displays the information about the stored green vegetable juice and allows a user to select the green vegetable juice s/he drank among the kinds of stored green vegetable juice when the stored green vegetable juice is made many times and 'Yes' is selected for the intake, thereby allowing the user to correctly know what kind of green vegetable juice s/he drank.

Therefore, the user terminal 20 may continuously generate intake history information about the green vegetable juice. The intake history information about the green vegetable juice may be collected in such a manner that push messages are used to inquire about a user's intake and receive an answer as given in the foregoing example. Alternatively, the intake history information about the green vegetable juice may be collected by obtaining a calendar history recorded by a user or obtaining information about whether a container (not shown) for storing the green vegetable juice is filled with the green vegetable juice (e.g., obtaining the information by receiving an image or weight information).

The user terminal 20 calculates a remaining amount and freshness of stored green vegetable juice based on a user's input about the intake (S14).

The user terminal 20 may calculate the weight of the stored green vegetable juice, for example, the weight of the remaining green vegetable juice by subtracting the intake weight from the weight of the extracted green vegetable juice in case where a user drank the green vegetable juice immediately after the juice extraction. For example, when a user drinks the green vegetable juice under a condition that the green vegetable juice weighs 500 g immediately after the juice extraction and once recommended intake of the green vegetable juice is generally 200 g, the weight of the remaining green vegetable juice is calculated as 300 g. Further, when a user makes selection by clicking an icon indicating specific green vegetable juice among the kinds of stored green vegetable juice through the push alarm generated at a certain time every day, the remaining amount may be calculated by subtracting the intake amount from the storage amount of the corresponding green vegetable juice.

Further, the user application may further include a detailed input page through which a user is allowed to set once intake amount, or input a detailed intake amount when the intake is increased or decreased beyond the set amount. When several family members drink one type of green vegetable juice or respectively drink customized types of green vegetable juice, the amount of green vegetable juice to be taken at one time may be subtracted whenever the icon indicating the corresponding green vegetable juice is clicked once. In this manner, it is easy to make selection about the intake The user terminal 20 selects at least one among the ingredients for green vegetable juice as the indicator ingredient. Here, the indicator ingredient refers to an ingredient susceptible to freshness or quality among the ingredients for the green vegetable juice. The memory 23 of the user terminal 20 is configured to store the function of change in quality versus change in time according to storage temperatures with respect to each of the ingredients for green vegetable juice. The processor 24 selects an ingredient, which is most susceptible to the quality at a storage temperature among the ingredients for the corresponding green vegetable juice, as the indicator ingredient. In this case, the storage temperature of the green vegetable juice may be previously set by a user. For example, three temperatures, e.g., freezing, refrigerating and room temperatures may be taken into account in case of a general storage place. A user may not only set the storage temperature in consideration of the freezing, refrigerating and room temperatures of his/her own refrigerator, but also set the temperature of the stored green vegetable juice as a default temperature (e.g., −18° C.) in consideration of his/her habit of storing the green vegetable juice. In this case, when the juice-extraction information is stored as received from the juicer 10 for green vegetable juice, the green vegetable juice is automatically stored based on the default temperature. Further, exceptionally, when the green vegetable juice is stored at the refrigerating temperature or the room temperature rather than the freezing temperature of −18° C. set as the default temperature, the storage temperature may be set by clicking detailed information of the corresponding green vegetable juice in the user application.

For example, when the storage temperature for first green vegetable juice is set to the refrigerating temperature, e.g., 2° C., and the ingredients for green vegetable juice include an apple, a carrot and a lemon, the processor 24 may select an ingredient, e.g., the apple, which is most susceptible to the freshness based on the function stored in the memory 23 related to change in quality of the ingredients for green vegetable juice at 2° C., as the indicator ingredient. The processor 24 calculates the freshness value and/or the remaining shelf life by substituting the storage period into the function related to the change in the quality of the indicator ingredient, i.e., the apple at 2° C., for example, by subtracting the juice-extraction time from the current time. Immediately after the juice extraction, the freshness may be calculated as 100%, and the remaining shelf life may be calculated as 3 days. The freshness and the remaining shelf life are varied depending on the storage temperature, the shelf life, etc., and may be calculated whenever a user executes the user application or checks the stored green vegetable juice in the menu of the user application. Further, the freshness value and the remaining shelf life are values related to each other, and the remaining shelf life may be determined based on the freshness value and the storage temperature. A function for calculating the remaining shelf life of each indicator ingredient may be separately established in advance, and the processor 24 may calculate the remaining shelf life with inputs of temperature, time, and a freshness value. Alternatively, the remaining shelf life corresponding to the freshness value and the storage temperature of each ingredient for green vegetable juice is tabulated and stored as a table in the memory 2, and the processor 24 may look up the remaining shelf life on the table.

According to an alternative embodiment of the disclosure, the processor 24 may give a score to change in freshness according to storage temperatures with regard to each of the ingredients for green vegetable juice, and calculate the freshness of the green vegetable juice by summing the scores. For example, the freshness based on change in the storage period according to the storage temperatures is scored and tabulated with regard to each of the ingredients for green vegetable juice and stored as a table in the memory 23, and the processor 24 calculates the freshness value by looking up and summing the scores corresponding to the storage temperature and time of the ingredients for the first green vegetable juice on the table. For example, when the storage temperature for the first green vegetable juice is set to the freezing temperature, e.g., −18° C., the storage period is 24 hours, and the ingredients for green vegetable juice include an apple, a carrot and a lemon, the processor 24 may calculate a freshness value of −6 and a remaining shelf life of 7 days by looking up and summing the scores, e.g., −3, −2 and −1 corresponding to the apple, the carrot and the lemon stored at −18° C. for 25 hours on the table. The remaining shelf life may be varied depending on the freshness value and the storage temperature. The function for calculating the remaining shelf life may be separately provided, and the table in which the remaining shelf life is tabulated corresponding to the freshness value and the temperature and stored in the memory 23 so that the processor 24 can look up the remaining shelf life on the table.

The user terminal 20 may generate and display information about the status of the stored green vegetable juice, which corresponds to change in the calculated weight and freshness of the green vegetable juice, as a smart button (S15).

Referring to FIG. 3, the user application includes menu items displayed at the top thereof, for example, self-check, recipe, effect check, lifehack information, setup, etc. Below the menu items, user information, family integration recipe, and status information about the stored green vegetable juice are displayed. The status information of the green vegetable juice is displayed in an area A, and smart buttons B indicating the status information of the green vegetable juice are displayed on the area A. FIG. 3 shows an example that there are three kinds of stored green vegetable juice. The smart button is generated corresponding to the juice extraction, and therefore a plurality of smart buttons may be displayed when the green vegetable juice of the same recipe is extracted at different times.

FIG. 4 illustrates an example of the smart button indicating the status information of the green vegetable juice. The smart button is represented with a shape and a color for intuitive understanding. The smart button includes a freshness display area indicating the freshness of the green vegetable juice, and a remaining-life display area indicating the remaining shelf life, and the processor 24 determines and generates the color of the freshness display area based on the calculated freshness value.

Referring to FIG. 4, the smart button may include a first color display area B1 in which the amount and freshness of the green vegetable juice are represented with color, a second color display area B2 in which the freshness and remaining shelf life of the green vegetable juice are represented with color, a first text area B3 in which information about the remaining shelf life is displayed, and a second text area B4 in which information about the ingredients for green vegetable juice are displayed.

The first color display area may be provided as an icon shaped like a bottle, and varied in color depending on the freshness of the green vegetable juice. The processor 24 stores color information corresponding to the freshness value, and identifies a color corresponding to the calculated freshness value. For example, FIG. 3 shows three colors of green, yellow and red to indicate the freshness. When the freshness value ranges from 0 to 10, the freshness values of 7 to 10 may be represented with green that indicates in safe, the freshness values of 4 to 6 may be represented with yellow that indicates in caution, and the freshness values of 1 to 3 may be represented with red that indicates in danger. In addition, a colored area in the icon shaped like a bottle corresponding to the first color display area indicates the remaining amount of green vegetable juice. FIG. 3 shows that almost 90% of the first color display area is pained in color, but FIG. 4 shows that only about 50% of the first color display area is pained in color. The colored area of the first color display area is varied depending on the remaining amount of green vegetable juice. In other words, the colored area is changed in proportion to the remaining amount of green vegetable juice. For example, the colored area in the icon shaped liked a bottle is enlarged as the amount of green vegetable juice increases, but reduced as the amount of green vegetable juice decreases.

In the second color display area, the freshness and remaining shelf life of the green vegetable juice are represented with color. Color filled in the area shaped like a ring is varied depending on the freshness value, and the size of the colored area is varied depending on the remaining shelf life. For example, the colored area becomes longer as the remaining shelf life increases, but becomes shorter as the remaining shelf life decreases. Thus, a user can intuitively know the freshness based on the color, and the remaining shelf life based on the length of the colored area.

A user can click the smart button corresponding to the stored green vegetable juice as shown in FIG. 3 to check the detailed information about the corresponding green vegetable juice. The detailed information about the green vegetable juice may include the date and time of juice extraction, a remaining amount, a storage temperature, an intake history (date and time), etc., which can be changed or modified by a user.

In the foregoing first embodiment, the information about the ingredients for green vegetable juice is identified and obtained by the image sensor of the juicer 10 for green vegetable juice. Alternatively, the information about the ingredients for green vegetable juice may be obtained from recipe information received from the service server 30.

Below, a smart system and method for providing green vegetable juice according to a second embodiment of the disclosure will be described with reference to FIGS. 1 and 5, in which repetitive descriptions to the foregoing embodiment are avoided as necessary.

Figure 5:
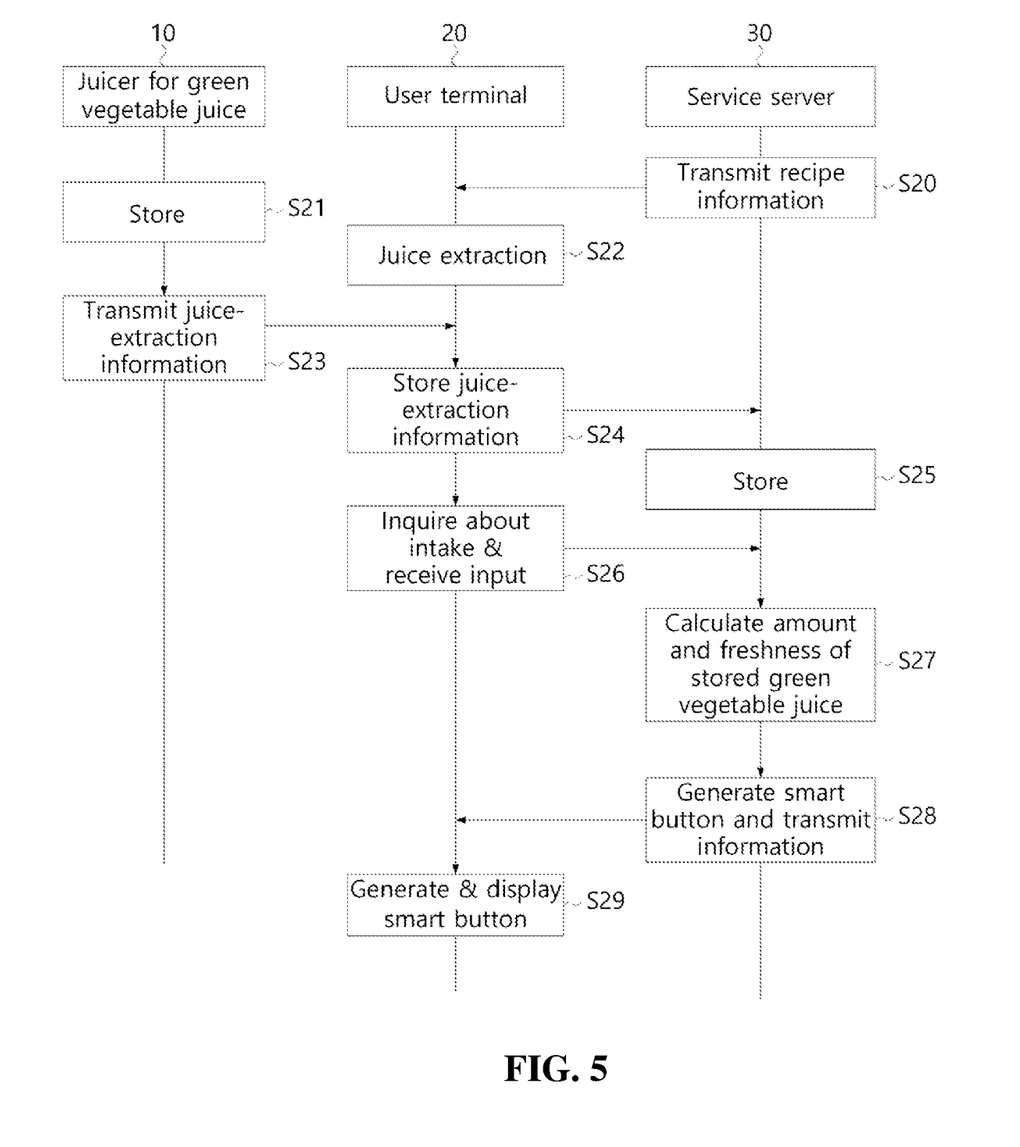
FIG. 5 is a flowchart showing an example of a smart method of providing information about green vegetable juice in a smart system for providing information about green vegetable juice according to the second embodiment of the disclosure.

FIG. 5 is a flowchart showing an example of a smart method of providing information about green vegetable juice in a smart system for providing information about green vegetable juice according to the second embodiment of the disclosure. The smart system for providing green vegetable juice according to this embodiment is different from that according to the first embodiment in that the service server 30 generates the ingredients for green vegetable juice, in other words, the recipe information, and calculates the freshness, etc. of the green vegetable juice. On the contrary to the foregoing first embodiment where the juicer 10 for green vegetable juice identifies the ingredients for green vegetable juice to be extracted through the image sensor and generates the juice-extraction information about the ingredients for green vegetable juice, this embodiment shows that the service server 30 generates the recipe information about the green vegetable juice and identifies the ingredients for green vegetable juice based on the recipe information.

The service server 30 generates a recipe for green vegetable juice, which is customized to a user, based on personal information that the user inputs through the user application. Here, the server 30 has an algorithm or AI model for generating the customized recipe for green vegetable juice based on an input of the personal information, in which the AI model may be established as it is subdivided and learns according to the effects of the green vegetable juice. The input for the AI model may include information about age, sex, disease, specific health conditions such as bowel habit, blood coagulation, distribution and mobility of red blood cells and white blood cells, etc., and a recipe for green vegetable juice customized to the input is provided as a result. The customized recipe information generated by the service server 30 may be transmitted to the user terminal 20 and/or the juicer 10 for green vegetable juice. In this embodiment, information about the ingredients for green vegetable juice is obtained on the premise that a user makes the green vegetable juice as instructed in the recipe provided by the service server 30.

The juicer 10 for green vegetable juice makes the green vegetable juice by extracting juice from the put ingredients as instructed in the customized recipe for the green vegetable juice provided by the service server 30; generates the juice-extraction information including at least one of time taken in making the green vegetable juice, identification information of the put ingredients, juice extraction conditions, and the customized recipe for green vegetable juice; and transmits the juice-extraction information to the user terminal 20. The user terminal 20 generates information about time when a user drinks the green vegetable juice, and information about intake history of the green vegetable juice based on the juice-extraction information of the extracted green vegetable juice. Such accumulated history information about the green vegetable juice may be stored in such a manner that intake time information, i.e., intake information in units of dates is stored like a calendar together with information about which recipe is used to make the green vegetable juice.

Referring to FIG. 5, the service server 30 generates the customized recipe information based on a user's input personal information, and transmits the generated customized-recipe information to the user terminal 20 (S20). The user terminal 20 receives and stores the recipe information (S21). Meanwhile, according to an alternative embodiment, the user terminal 20 may obtain information about the ingredients for green vegetable juice based on the received recipe information.

When juice is extracted in the juicer 10 for green vegetable juice (S22), the juicer 10 for green vegetable juice generates and transmits the juice-extraction information including the juice-extraction time, the juice-extraction amount, etc. to the user terminal 20 (S23).

The user terminal 20 stores and transmits the received juice-extraction information to the service server 30 (S24). The service server 30 generates and stores the juice-extraction information, which is received via the user terminal 20, as the juice-extraction history information (S25).

The user terminal 20 generates a push alarm for inquiring about the intake of the green vegetable juice, receives an answer to the inquiry about the intake from a user, generates the answer as the intake information, and transmits the intake information to the service server 30.

The service server 30 may obtain the ingredients for green vegetable juice based on the recipe information, and calculates the amount, freshness, remaining shelf life, etc. of the stored green vegetable juice based on the juice-extraction information and the intake information which are received from the user terminal 20 (S27). In addition, the service server 30 generates the smart buttons based on the status information such as the amount, freshness, remaining shelf life, etc. of the stored green vegetable juice, and provides the smart buttons to the user terminal 20 (S28).

The user terminal 20 generates and displays the smart buttons showing the status of the stored green vegetable juice on the user interface 21 based on the smart button information received from the service server 30 (S29).

In the foregoing second embodiment, the ingredients for green vegetable juice are obtained based on the recipe information. Alternatively, the information about the identified ingredients for green vegetable juice may be received from the juicer 10 for green vegetable juice, and the freshness of the green vegetable juice may be calculated based on the received information about the identified ingredients.

Figure 6:
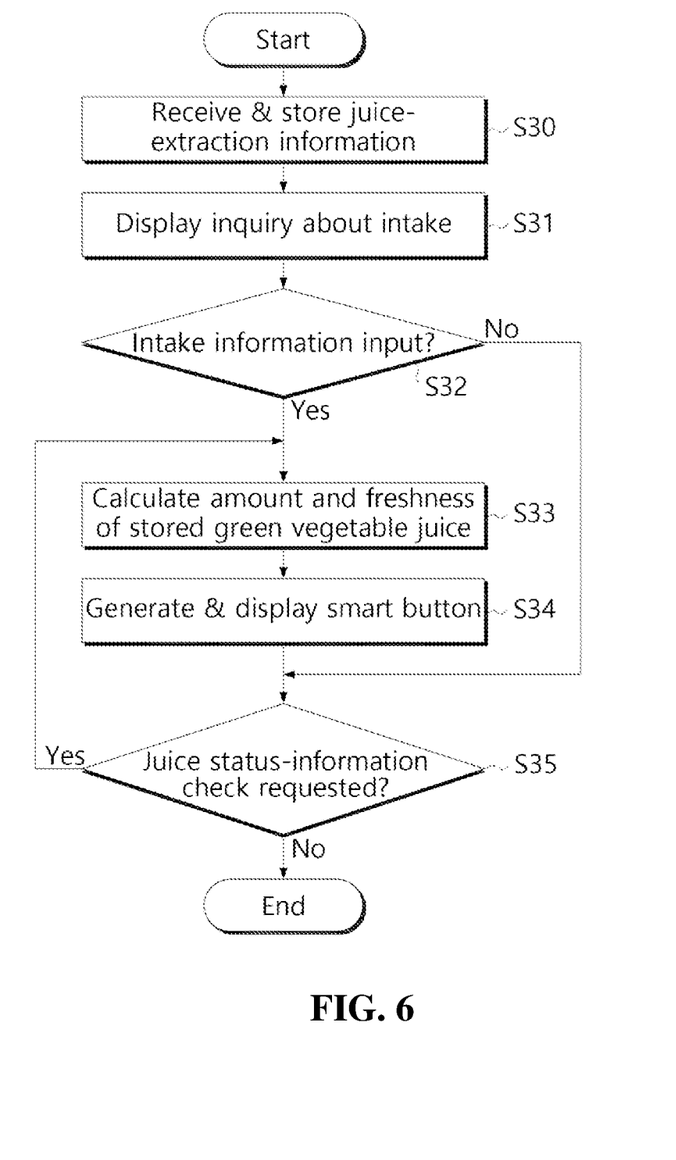
FIG. 6 is a flowchart showing a smart method of providing information about a status of green vegetable juice in a user terminal according to a third embodiment.

FIG. 6 is a flowchart showing a smart method of providing information about a status of green vegetable juice in a user terminal according to a third embodiment, in which repetitive descriptions to the foregoing embodiment are avoided as necessary.

The user terminal 20 receives and stores the juice-extraction information about the juice-extraction time, the amount of green vegetable juice, the ingredients for green vegetable juice, etc. from the juicer 10 for green vegetable juice (S30). The user terminal 20 displays a push alarm based on inquiry about the intake of the green vegetable juice (S31); calculates a current remaining amount of green vegetable juice by subtracting an intake amount from the extracted amount of green vegetable juice when a user inputs that s/he drank the green vegetable juice; checks the ingredients for green vegetable juice, the storage temperature, etc.; and calculates the freshness and the remaining shelf life based on the time stored in the memory 23 and the function of change in quality versus change in time and temperature stored in the memory 23 with regard to each of the ingredients for green vegetable juice (S33). The freshness may be calculated by a method of selecting the indicator ingredient and calculating the freshness based on the selected indicator ingredient, or may be calculated based on a table in which freshness scores are tabulated according to the temperatures and times of the ingredients.

The user terminal 20 generates and displays the smart button based on the calculated freshness value, remaining amount, remaining shelf life, ingredients for green vegetable juice, etc. of the green vegetable juice (S34).

When a user executes an app or selects a status information check of the stored green vegetable juice in the menu of the executed app (S35), the user terminal 20 performs the processes of S33 to S34, thereby informing a user of the freshness information about the stored green vegetable juice.

On the other hand, in a case where a user answers that s/he did not drink the green vegetable juice (S32), when the user executes an app or selects a status information check of the stored green vegetable juice in the menu of the executed app (S35), the user terminal 20 performs the processes of S33 to S34 and informs a user of the freshness information about the stored green vegetable juice.

In the foregoing embodiments, the freshness calculation and the smart button generation are carried out after the user terminal 20 inquires the intake of the green vegetable juice and receives the answer. Alternatively, the processes of calculating the freshness and generating the smart button may be carried out immediately after the juice extraction.

In the foregoing description, all elements according to an embodiment of the disclosure are combined or operate as combined, but the disclosure is not limited to this embodiment. In other words, within the scope of the disclosure, one or more among all the elements may be selectively combined and operate. Further, each of all the elements may be embodied as independent hardware, but some or all of the elements may be selectively combined and embodied as a computer program having a program module for implementing some or all functions combined in one or a plurality of hardware components. The codes and code segments of the computer program may be easily inferred by those skilled in the art. Such a computer program may be stored in a computer readable media and read and executed by a computer to thereby implement the embodiments of the disclosure. The media of the computer program may include a magnetic recording medium, an optical recording medium, etc.

Further, the terms "comprise", "include", "have" or the like mean that corresponding elements may be included unless otherwise mentioned, and thus construed as not excluding but including other elements. Unless otherwise defined, all terms including technical or scientific terms have the same meanings as generally understood by a person having ordinary knowledge in the field of the art to which the disclosure pertains. Terms generally used like terms defined in a dictionary should be interpreted to coincide with the contextual meaning of the related art, and shall not be construed in an ideal or excessively formal sense unless explicitly defined in the disclosure.

The foregoing descriptions are merely for illustrative purpose only, and various modifications and changes can be made by those skilled in the art without departing from the essential characteristics of the disclosure. Therefore, the embodiments of the disclosure are not intended to limit the technical idea of the disclosure but to describe the disclosure, and the scope of disclosure is not limited by these embodiments. The scope of the disclosure should be interpreted by the following claims, and all technical ideas within the equivalent scope should be interpreted as being included in the scope of the disclosure.

As described above, a smart system and method for providing information about green vegetable juice according to the disclosure calculate the amount and freshness of stored green vegetable juice and allow a user to intuitively know the amount and freshness.

Further, an indicator ingredient having representativeness is selected among ingredients for green vegetable juice, and the freshness and remaining shelf life of the green vegetable juice are calculated based on a freshness changing function of the indicator ingredient, thereby simply and accurately reflecting the freshness of the green vegetable juice.

What is claimed is:

1. A smart system for providing information about green vegetable juice, the system comprising:
   a juicer for green vegetable juice, configured to extract juice from ingredients for green vegetable juice, and generate and transmit juice-extraction information which comprises juice-extraction time of the green vegetable juice and weight of the green vegetable juice;
   a user terminal including a processor, configured to receive the juice-extraction information from the juicer for green vegetable juice, receive intake information of the green vegetable juice from a user, and generate and display a smart button with status information about stored green vegetable juice depending on change in weight and freshness of the stored green vegetable juice based on the juice-extraction information and the intake information; and
   a service server configured to generate recipe information about the green vegetable juice and provide the recipe information to at least one of the user terminal and the juicer for green vegetable juice,
   wherein the user terminal is configured to receive the recipe information from the service server or the juicer for green vegetable juice, and obtain information about the ingredients for green vegetable juice based on the recipe information, and
   wherein at least one of the service server and the user terminal is configured to select at least one among the ingredients for green vegetable juice as an indicator ingredient based on susceptibility to quality at a storage temperature, and calculate a freshness value and a remaining shelf life of the green vegetable juice depending on a storage period of the green vegetable juice or the storage period and a storage temperature based on a freshness changing function of the indicator ingredient which is a function of change in quality versus change in time according to the storage temperature of the indicator ingredient.

2. The system according to claim 1, wherein
   the smart button comprises a freshness display area for indicating the freshness of the green vegetable juice, and a remaining-life display area indicating the remaining shelf life; and
   the user terminal is configured to determine and display a color of the freshness display area based on the calculated freshness value.

3. The system according to claim 2, wherein the user terminal is configured to generate a user interface to receive an input about intake of the green vegetable juice, calculate the weight of the stored green vegetable juice based on the input about the intake of the green vegetable juice, and reduce a colored area in the freshness display area of the smart button in size in proportion to the calculated weight of the stored green vegetable juice.

* * * * *